United States Patent
Zhang

[11] Patent Number: 5,814,308
[45] Date of Patent: Sep. 29, 1998

[54] METHODS FOR THE TREATMENT OF GASTROINTESTINAL TRACT DISORDERS

[76] Inventor: Ke Zhang, 2146 Peak Pl., Thousand Oaks, Calif. 91362

[21] Appl. No.: 622,720

[22] Filed: Mar. 26, 1996

[51] Int. Cl.⁶ .......................... A61K 38/18; A61K 38/19; A61K 38/20; A61K 38/30

[52] U.S. Cl. .......................... 424/85.1; 424/85.2; 514/12; 514/21

[58] Field of Search .................................. 514/12, 8, 21; 424/85.1, 85.2; 530/350, 351, 395

[56] References Cited

U.S. PATENT DOCUMENTS

| | | | |
|---|---|---|---|
| 5,219,991 | 6/1993 | Leonard et al. | 530/351 |
| 5,234,908 | 8/1993 | Szabo et al. | 514/12 |
| 5,315,000 | 5/1994 | Degen | 536/23.5 |

FOREIGN PATENT DOCUMENTS

| | | |
|---|---|---|
| WO 92/02246 | 2/1992 | WIPO . |
| WO 92/03155 | 3/1992 | WIPO . |
| WO 93/07891 | 4/1993 | WIPO . |
| WO 93/14783 | 8/1993 | WIPO . |
| WO 93/25227 | 12/1993 | WIPO . |
| WO 94/05318 | 3/1994 | WIPO . |
| WO 94/06420 | 3/1994 | WIPO . |
| WO 94/28133 | 12/1994 | WIPO . |
| WO 95/28963 | 11/1995 | WIPO . |

OTHER PUBLICATIONS

Gaudino et al., Oncogene 11, 2627–2637 (1995) (Abstract only).
Thomas et al., GUT 35, 1742–1746 (1994) (Abstract only).
Burgess et al., J. of Gastroentenol–Hepatol. 5, 10–21 (1990).
Carson, *Histotechnology: A Self–Instructional Text* American Society of Clinical Pathologist Press pp. 158–160 (1990).
Degen et al., Biochemistry 30, 9781–9791 (1991).
Falk et al. Am. J. Physiol. 266, G987–1003 (1994).
Fausset and Lu Electrophoresis 12, 22–27 (1991).
Gaudino et al. EMBO J. 13, 3524–3532 (1994).
Gordon et al., FASEB 6, 3039 (1992).
Harlow and Lane *Antibodies: A Laboratory Manual*, Cold Spring Harbor Laboratory Press, Cold Spring Harbor, NY (1988). (Table of Contents Only).
Housely et al., J. Clin. Invest. 94, 1764–1777 (1994).
Johnson et al., J. Cell Biol., 118, 741 (1992).
Kuniyashi et al., Jpn. J. Cancer Res. 82, 969 (1991).
Leonard et al. Exp. Cell Res. 114, 117 (1978).
Leonard et al. Exp. Cell. Res. 102, 434 (1976).
Malden et al. Int. J. Cancer 43, 380 (1989).
Merewether et al. in *Techniques in Protein Chemistry VI*, pp. 153–160 (1995).
Podolsky, Am. J. Physiol. 246, G179 (1993).
*Remington's Pharmaceutical Sciences*, 18th ed. Gennaro, ed. Mack, Easton, PA (1990) (Table of Contents Only).
Ronsin et al. Oncogene 8, 1196–1202 (1993).
Wang et al. Science 266, 117–119 (1994).
Whitehead et al. In Vitro Cellular & Developmental Biology, 23, 436–442 (1987).
Whitehead, Cancer Res. 47, 2683 (1987).

*Primary Examiner*—Jeffrey E. Russel
*Attorney, Agent, or Firm*—Robert B. Winter; Ron K. Levy; Steven M. Odre

[57] ABSTRACT

Methods for treating gastrointestinal tract disorders by protection, regeneration and repair of intestinal epithelium are described. Macrophage stimulating protein is found to promote colony formation by crypt cells and may be involved in stimulating proliferation of intestinal crypt cells. Also described are pharmaceutical compositions for MSP and methods for identifying substances that stimulate crypt cell proliferation.

10 Claims, 12 Drawing Sheets

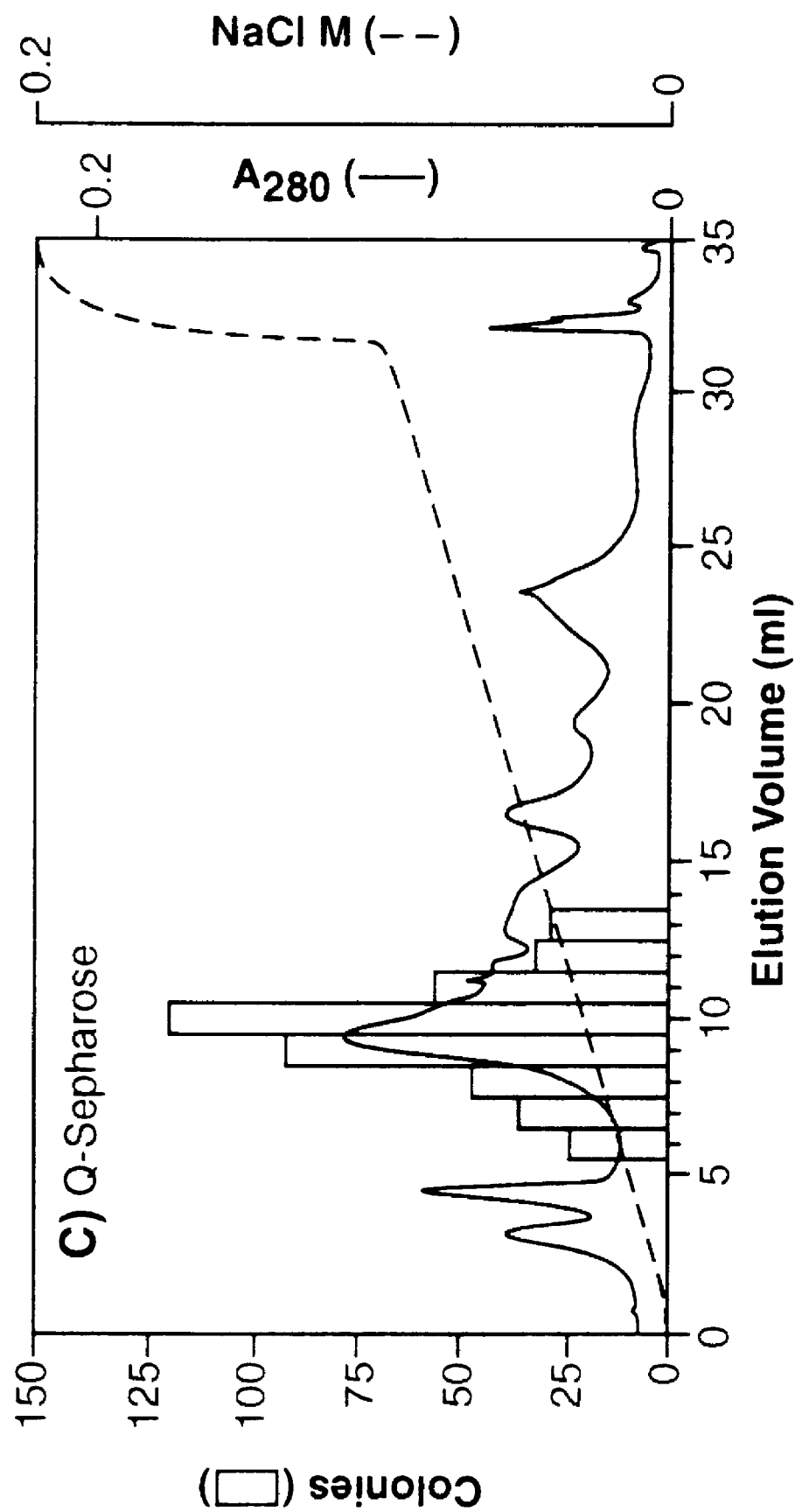

FIG. 6

| Peptide | Sequence | Human MSP |
|---|---|---|
| Derived from p55 | | |
| T43a | SPLNDFQVLR | 21- 30 |
| T5 | FPNDHK | 138-143 |
| T43b | NPDGDPGGP | 159-177 |
| T25.8 | FTPTLR | 144-149 |
| T40.8 | EF(C)DLPR | 261-267 |
| T38.9 | NPDGSEAPW(C)FTQR | 334-347 |
| T49.6 | NPDGDSHGPW(C)Y | 421-437 |
| T26.5 | WDAQLPHQHR | 307-317 |
| T35.8a | WDLQHPHPHPFEPGK | 215-229 |
| T35.8b | (C)GSEAPQQEATTLNCFR | 268-285 |
| Derived from p22 | | |
| NH₂ | VVGGQPGNSPWTVSLRNRQGQHFXGGSLV | 484-512 |
| T36 | LERPVILNQR | 574-583 |
| T25.9 | YVVPPGTR | 594-601 |
| T36.4 | (C)EIAGWGES | 602-611 |
| T50 | VSVFVDWKHK | 697-707 |

FIG. 8

```
Peptides                        T26.5  WDAQLPHQHR              T38.9  NPDGSEAP
                                       ||||||||||                     ||||||||
bovine MSP    FRGKGEGYRGTVNTTAAGVPCQRWDAQLPHQHRFAPEKYACKDLRENFCRNPDGSEAP
              ||||||||||| |||| |||||||||||||||| |||||||||||||||||||||||||
human MSP     FRGKGEGYRGTANTTTAGVPCQRWDAQIPHQHRFTPEKYACKDLRENFCRNPDGSEAP
              290       300       310       320       330       340

WCFTQR
              ||||||
              WCFTSRPGMRMAFCYQIRRCTDDVRPEDCYHGAGELYRGSVSKTRKGIRCQNWSAETP
              |||| ||||||  ||||||||||||| |||||||||  ||||||||| ||||||||
              WCFTLRPGMRAAFCYQIRRCTDDVRPQDCYHGAGEQYRGTVSKTRKGVQCQRWSAETP
              350       360       370       380       390

T49.6  NPDGDSHGPWCY
                                         ||||||||||||
              HKPQFKHTSAPHTPLEENFCRNPDGDSHGPWCYTTDPGTPFDYCALRRCDDDQQPSIL
              |||| |||| |||| ||||||||||||||||||| |||| |||||||||  |||||||
              HKPQFTFTSEPHAQLEENFCRNPDGDSHGPWCYTMDPRTPFDYCALRRCADDQQPPSIL
              400       410       420       430       440       450

NH2  VVGGQPGNSPWTVSLRN
                                 |||||||||||||||||
              ETAHQVLFDKCGKRVTRVDPLHSKLRVVGGQPGNSPWTVSLRN
              ||  |||||||||||||| | |||||||| ||||||||||||
              DPPDQVQFEKCGKRVDRLDQRRSKLRVVGGHPGNSPWTVSLRN
              460       470       480       490       500
```

METHODS FOR THE TREATMENT OF GASTROINTESTINAL TRACT DISORDERS

FIELD OF THE INVENTION

The invention relates generally to factors which modulate the growth and differentiation of epithelial cells of the gastrointestinal tract. More particularly, the invention relates to a factor, macrophage stimulating protein (MSP), which stimulates colony formation by crypt cell and may stimulate the proliferation of colon crypt cells. MSP may protect, repair or regenerate intestinal epithelium and therefore may be useful in the treatment of disorders of the gastrointestinal tract.

BACKGROUND OF THE INVENTION

The gastrointestinal tract, which includes the stomach, small intestine and large intestine, is lined with a single layer of epithelial cells (the mucosa). In the intestine, this layer protects a highly convoluted surface consisting of villi, or projections into the lumen of the gut, and crypts, which penetrate into the underlying connective tissue.

The intestinal epithelium is a highly proliferative tissue that is continually renewed throughout adult life. Current concepts of what is known about intestinal epithelial proliferation and differentiation has been briefly reviewed (Podolsky, Am. J. Physiol. 246, G179 (1993)). It is generally felt that crypt stem cells give rise to rapidly proliferating progenitor cells capable of differentiating into one of four distinct lineages: enterocyte, goblet, enteroendocrine and paneth cells. There appears to be a dynamic equilibrium between crypt cell production and the senescence and exfoliation of highly differentiated epithelial cell types. The teleological significance of constitutive renewal is not clear, but it is thought to prevent the accumulation of mutations which could disrupt cell growth regulation. Normal intestinal epithelial growth regulation is thought to be regulated in part by soluble factors that stimulate mitogenesis, and in part by extracellular matrix proteins and adjacent mesenchyme-derived, pericryptal fibroblasts. The steps leading to terminally differentiated cell types from multipotent stem cells are not known, and specific markers identifying progenitor cell populations committed to various lineages have not been identified.

Using transgenic and chimeric mice, several essential properties of stems cells have been illuminated as a paradigm for self-renewing and regenerating tissues (Gordon et al., FASEB 6, 3039 (1992)). First, since crypt epithelium is monoclonal in nature, the stem cells must divide asymmetrically, producing a self-renewing stem cell, and a progenitor cell committed to production of all differentiated cell types. Second, the daughter stem cell must have enormous proliferative capacity. Third, the stem cell must be functionally retained within the crypt niche and therefore have specific contacts with the lamina propria and/or other adjacent cells. The nature and identity of the intestinal epithelial stem cell remains to be elucidated.

To help address the nature of intestinal epithelial differentiation, in vitro systems have been developed using cell lines derived from intestinal epithelium. See, for example, Whitehead et al. (Cancer Res. 47, 2683 (1987)). Several autocrine factors have been identified in colon carcinoma cell lines which may be important for supporting regeneration of the colonic mucosa. Among the factors produced by these cell lines is TGFα (Malden et al. Int. J. Cancer 43, 380 (1989)) and members of the EGF family, amphiregulin (Kuniyashi et al., Jpn. J. Cancer Res. 82, 969 (1991)) and cripto (Johnson et al., J. Cell Biol., 118, 741 (1992)), the latter having also been expressed in normal colonic mucosa. However, it is not known if the EGF-related proteins stimulate the growth of normal crypt cells. In addition, it is speculated that lymphokines may be involved in the hyperproliferation of the mucosa that is characteristic of inflammatory bowel disease.

Presently, very little is known about the factors that direct the proliferation of crypt cells leading to renewal of the intestinal epithelium. Knowledge in this area has been hampered by the lack of assays which measure the effects of growth factors on crypt stem cells.

A number of disorders of the gastrointestinal tract are characterized by damage or depletion of intestinal or colonic mucosa resulting from exposure to environmental agents or from inflammatory responses, autoimmune diseases, infection, or physical injuries.

Patients receiving radiation therapy and chemotherapy for cancer frequently experience marrow toxicity resulting in anemia and leukopenia. Marrow toxicity is often associated with aggressive treatment regimens that call for elevated doses of radiation or chemotherapeutic drugs. Until recently, dose reduction or cessation of treatment was generally required until red blood cell and white blood cell levels were restored. However, the introduction of factors which enhance hematopoiesis such as erythropoietin (EPO) and granulocyte colony stimulating factor (G-CSF) into the treatment regimen has greatly alleviated this source of toxicity.

The second most common source of toxicity associated with cancer therapy is gut toxicity which is characterized by a depletion of the intestinal epithelium. Currently, there are no factors available which will protect or restore the gut lining during cancer therapy. The availability of factors for alleviating this side effect of cancer therapy would be desirable.

Disorders of the lower bowel (distal ileum and colon) can also adversely affect the intestinal mucosa and include a class of diseases referred to as inflammatory bowel disease. Two major diseases are ulcerative colitis and regional enteritis (Crohn's disease). Ulcerative colitis is an inflammation of the mucosal and submucosal lining in the colon and rectum while Crohn's disease is characterized by inflammation which can involve all layers of the gut. Other forms of inflammatory bowel disease include regional ileitis and proctitis. Current treatment for inflammatory bowel disease includes anti-inflammatory drugs and, if necessary, surgery to remove the affected tissues.

The following references describe examples of various treatments for gastrointestinal disorders:

WO 94/06420 describes the use of osteogenic proteins, such as OP-1, OP-2 and CBMP2 proteins, and related proteins such as DPP, Vg1, Vgr-1, 60A and GDF-1 for the treatment of gastrointestinal ulcers.

WO 94/05318 describes the use of interleukin-11, interleukin-6, leukemia inhibitory factor, oncostatin M and ciliary neurotrophic factor for the treatment of damaged or depleted epithelial cells of the small and large intestine. The treatment may also be used for liver epithelial cells, skin cells, hair cells and sperm cells.

WO92/03155 describes compositions of glutamine, or a derivative or analog thereof, a short or medium chain fatty acid, and a growth factor or analog thereof, which can be used for treatment of the intestinal mucosa. The growth factor can be growth hormone, insulin-like growth factors 1 and 2 (IGF-1 and IGF-2), growth hormone releasing factors, or analogs thereof.

WO 93/25227 describes the use of IGF-2 for the treatment of gastrointestinal disorders.

U.S. Pat. No. 5,235,908 describes the use of platelet derived growth factor (PDGF) for the treatment of gastrointestinal ulcers.

WO 93/07891 describes the use of epidermal growth factor (EGF) compositions for the treatment of gastrointestinal disorders such as inflammatory bowel disease and colitis.

WO 92/02246 and WO 93/14783 describe the use of nicked or non-nicked species of human EGF1-48 or EGF1-47 or EGF1-49 congeners for treating abnormal growth conditions including gastrointestinal lesions.

The above references describe factors which stimulate the proliferation of many different types of epithelial cells, including those in the gut. However, there are no reports of factors which stimulate the proliferation of colonic crypt cells from which all intestinal epithelial cell types arise. Such factors are useful for treating a variety of gastrointestinal disorders, including disorders in which stimulation of epithelial cell growth outside the gut is not desirable.

It is therefore an object of the invention to identify factors which modulate the growth and/or differentiation of intestinal epithelial cells.

It has been found that a previously identified protein termed macrophage stimulating protein, or MSP, has the activity of stimulating colony formation by colonic crypt cells in culture. This is the first report of a factor which acts on normal crypt cells. These findings implicate MSP as a therapeutic for the regeneration of damaged or depleted intestinal epithelium.

SUMMARY OF THE INVENTION

The invention relates to methods for treating disorders of the gastrointestinal tract by administering a therapeutically effective amount of macrophage stimulating protein, or MSP. MSP stimulates colony formation by crypt cells and may also stimulate proliferation of crypt stem cells. In this respect, MSP is particularly useful for elevating production of all intestinal epithelial cell types. Therefore, the invention may be used to protect, repair or regenerate the intestinal epithelium which has been damaged or has potential to be damaged as a result of cancer therapy, physical injury or disease.

The invention also provides for pharmaceutical compositions of MSP in a pharmaceutically acceptable diluent, adjuvant, preservative, carrier or stabilizer. MSP is also provided in formulations suitable for the route of delivery being used.

DESCRIPTION OF THE FIGURES

FIGS. 4A–4C. Purification of a crypt colony forming activity from KG-1 conditioned medium. Conditioned medium was harvested from cells, clarified, then fractionated by chromatography over various columns. A) Heparin-Sepharose; B) Phenyl-Sepharose; C) Q-Sepharose. Concentration of elution buffer is marked by a hatched line, and total protein by a solid line. Crypt colony forming activity is indicated by solid bars.

FIG. 6. Amino acid sequencing of the crypt colony forming factor. The p55 and p22 peptides from the p75 protein were separated by SDS-PAGE, and digested with trypsin. The resulting peptides were separated by a C4 column using HPLC system. The sequences of the N-terminal of the p22 protein band, and selected trypsin peptides were determined and are shown in the figure. The sequences obtained share homology with those of human MSP. The locations of sequences in human MSP which share homology with these sequences are indicated. The residues in bold face differ from the corresponding residues in human MSP.

FIG. 8. Amino acid sequence alignment of bovine and human MSP. The nucleotide sequence was obtained from bovine MSP cDNA which had been PCR amplified from bovine liver RNA. The deduced amino acid sequence is shown. The bottom line is the amino acid sequence of human MSP. The top line is the peptide sequences which match this region.

DETAILED DESCRIPTION OF THE INVENTION

As used herein, the term "gastrointestinal tract" refers to the stomach, small intestine and large intestine. The "lining of the gastrointestinal tract" refers to the layer of epithelial cells exposed to the lumen of the stomach and intestine. The term "intestine" refers to that portion of the alimentary canal extending from the pyloric opening of the stomach to the anus and is also referred to as the bowel or gut. The term "colon" refers to that section of the large intestine extending from the cecum to the rectum.

Stem cells resident in intestinal crypts are capable of dividing without limit and the resulting daughter cells may remain as stem cells or may differentiate to mature intestinal epithelial cell types. Crypt cell preparations are not viable in culture and will not form colonies in the absence of factors which stimulate proliferation. It has been observed that the presence of 10% fetal bovine serum (FBS) will stimulate colony formation by mouse crypt cell preparations (see Example 1). This forms the basis for an assay to identify factors which may have activity on crypt cells. A number of purified growth factors were tested in the colony forming assay and all of those tested, except for neu differentiation factor-β1 (NDF-β1), failed to show any activity (see FIG. 2). The extent of colony formation stimulation by NDF-β1 was similar to that seen for 10% FBS. NDF-β1 is described in PCT Application No. WO 94/28133 which is incorporated by reference.

Conditioned media containing 0.5% FBS from various cell lines were screened for the ability to stimulate colony formation by colonic crypt cells. It was observed that medium from KG-1 cells stimulated colony formation. The extent of stimulation by KG-1 cells was comparable to that observed for growth medium containing 10% FBS and was significantly greater than colony stimulation by any other conditioned medium tested (See FIG. 3 for a comparison of some of the media tested). The crypt colony forming activity was purified by heparin sepharose, phenyl sepharose and Q-sepharose chromatography (Example 2 and FIG. 4). The purified factor was observed to have a molecular weight of about 75 kdal on non-reducing SDS-polyacrylamide gels and migrated as two bands of 55 kdal and 22 kdal on reducing SDS-polyacylamide gels (see FIG. 5). Amino acid sequencing revealed that the purified factor had a high degree of homology to human macrophage stimulating factor (MSP) and it was further confirmed to be the bovine homolog of human MSP (Example 3). Thus the colony forming activity observed on crypt cells was likely due to the presence of MSP in the fetal bovine serum. Since growth medium containing 0.5% FBS shows negligible colony forming activity, it is possible that a factor secreted from KG-1 cells processes a MSP precursor present in conditioned medium. Alternatively, MSP present in the normal growth medium may bind to the surface matrix of KG-1 cells, and be released later into the conditioned medium.

Figure 2:
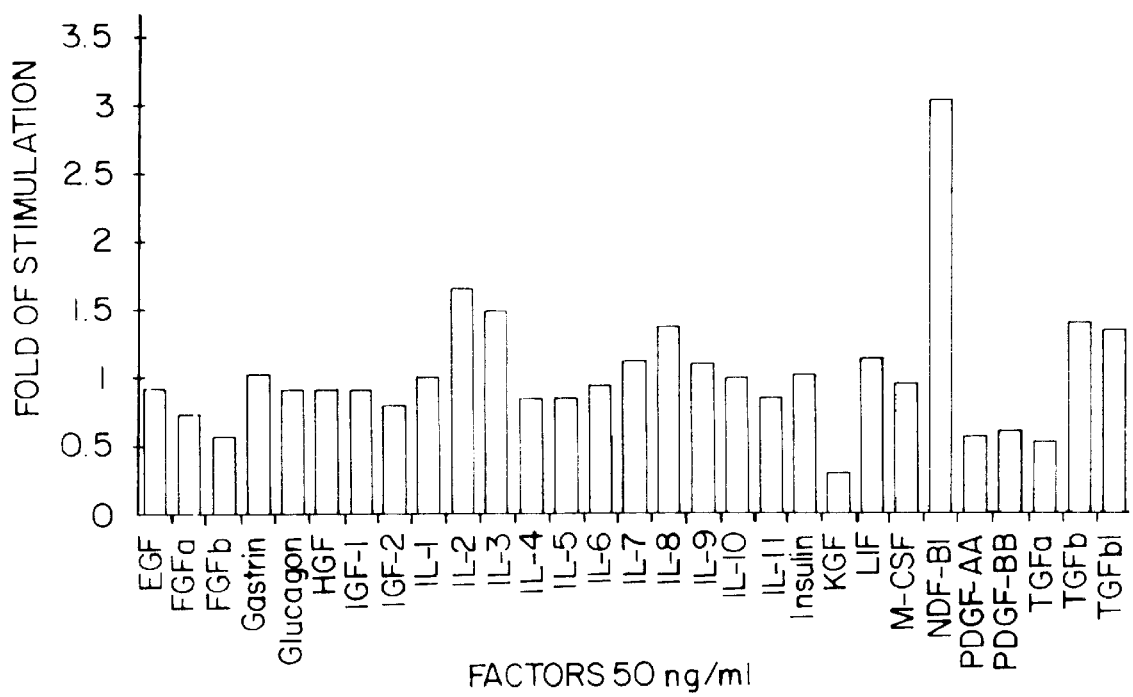
FIG. 2. Testing of known factors in crypt colony formation assay. Crypts were incubated in the presence of factors at 50 ng/ml for 24 hours at 37° C. The number of colonies on the plates of treated crypts were compared to that of untreated crypts. The activities are shown as fold of stimulation. The results shown in this figure are based on one experiment. The screen was repeated twice, and similar results were obtained.

This is the first report of a polypeptide factor which acts on normal crypt cells. The significance of this finding is two-fold. First, cells isolated from intestinal crypts contain stem cells which give rise to all mature intestinal epithelial cell types. Thus stimulation of crypt colony formation may correlate with a stimulation of crypt stem cell proliferation which, in turn, leads to an increase in the population of all mature intestinal epithelial cell types. This biological activity is likely to be important in repopulating epithelial linings which have been damaged or depleted. Second, it has been observed that crypt cells express a multitude of cell surface receptors, including receptors for epidermal growth factor, basic fibroblast growth factor-1, hepatocyte growth factor, insulin-like growth factor-1, HER-2/neu, keratinocyte growth factor and ECK. (Burgess et al., J. of Gastroentenol-Hepatol. 5, 10–21 (1990); Housely et al., J. Clin. Invest. 94, 1764–1777 (1994)). Yet, crypt cells do not appear to respond to the ligands which are known to interact with and activate these receptors (FIG. 2). Thus, the interaction of MSP with its receptor on the surface of crypt cells is unique in its ability to generate a biological response in crypts.

MSP has been previously identified as an activity present in mammalian blood plasma which makes mouse peritoneal macrophages responsive to chemoattractants such as complement C5a (Leonard et al. Exp. Cell. Res. 102, 434 (1976); Leonard et al. Exp. Cell Res. 114, 117 (1978). Purified MSP was obtained from human serum as described in U.S. Pat. No. 5,219,991 and DNA encoding human MSP was reported in U.S. Pat. No. 5,315,000. MSP was referred to as an hepatocyte growth factor (HGF)-like protein based upon its homology to HGF and its activity in promoting proliferation of hepatocytes. Recently, it has been reported that MSP is a ligand for ron, a cell membrane protein tyrosine kinase which is a member of the c-met family of protein tyrosine kinases (Wang et al. Science 266, 117–119 (1994); Gaudino et al. EMBO J. 13, 3524–3532 (1994); Ronsin et al. Oncogene 8, 1195–1202 (1993)). The expression of RON in human tissues and cell lines was examined (Gaudino et al., ibid) and RON was found to be expressed in colon, skin, lung and bone marrow, and in granulocytes and adherent monocytes. Epithelial cell lines derived from gastric, pancreatic and mammary carcinoma, and hematopoietic cell lines also showed RON expression. MSP induced tyrosine phosphorylation of RON and stimulated DNA synthesis in a mammary carcinoma cell line. These observations suggest that MSP may exhibit biological activity other than macrophage activation, but the nature of MSP activity other than activating macrophages has remained elusive. In particular, it was not previously known that MSP had activity related to the proliferation of intestinal epithelial cells.

The invention provides for the treatment of disorders of the lining of the gastrointestinal tract by administration of a therapeutically effective amount of MSP. The treatment provided herein is particularly useful for disorders involving the intestinal epithelium. The factors of the present invention can modulate the proliferation or differentiation of intestinal epithelium, thereby protecting healthy epithelium from damage and inducing repair and/or regeneration of damaged or depleted epithelium. Administration of MSP may occur prior to, concurrent with, or after the onset of a disorder of the gastrointestinal tract lining for a time and a concentration sufficient to protect, repair and/or regenerate the gut lining.

As used herein, a "therapeutically effective amount" refers to that amount of MSP which provides a therapeutic effect for a given condition and administrative regimen. Said amount may vary from 0.1 μg/kg body weight to 1000 mg/kg body weight and may be more precisely determined by one skilled in the art.

Efforts to aggressively treat cancer have led to the administration of higher doses of chemotherapeutic agents or the use of whole body radiation, but such regimens can lead first to bone marrow toxicity (depletion of red blood cells and white blood cells) followed by gut toxicity (depletion of intestinal epithelium). It is usual that a dose reduction or a cessation of therapy occurs until the toxicity is overcome. A preferred method of treatment is the use of MSP as an adjunct to chemotherapy or radiation therapy, either prior to or concurrent with such therapy. MSP may help maintain or repair epithelial cell linings in the intestinal tract and thereby prevent or reduce the occurrences of reduction or cessation of therapy.

Certain disease states may also lead to damage or depletion of intestinal epithelium and may be treated by administration of MSP. Examples include inflammatory bowel disease, a class of diseases including ulcerative colitis and Crohn's disease, duodenal ulcers or infections. Administration of MSP will help restore normal intestinal mucosa where damage has occurred.

It is understood that MSP may be used alone or in conjunction with other factors for the treatment of intestinal epithelial disorders. In one embodiment, MSP is used in conjunction with a therapeutically effective amount of a factor which promotes epithelial cell growth. Such factors include insulin growth factor-1 (IGF-1), insulin growth factor-2 (IGF-2), epidermal growth factor (EGF), transforming growth factor-α (TGF-α), acidic and basic fibroblast growth factor (FGF), platelet derived growth factor (PDGF), keratinocyte growth factor (KGF), interleukin-6 (IL-6) or interleukin-11 (IL-11). In another embodiment, MSP, when used as an adjunct to chemotherapy or radiation therapy to alleviate gut toxicity, may be administered in conjunction with a hematopoietic factor such that marrow toxicity may be alleviated as well. The hematopoietic factors to be used in conjunction with MSP include erythropoietin (EPO), granulocyte colony stimulating factor (G-CSF), megakaryocyte growth and differentiation factor (MGDF), granulocyte macrophage colony stimulating factor (GM-CSF), stem cell factor (SCF), interleukin-3 (IL-3) or interleukin-6 (IL-6).

MSP may be administered by a variety of routes including parenteral, oral, nasal or rectal administration. Parenteral administration may occur by intravenous, subcutaneous, intradermal, intramuscular, intraarcticular and intrathecal injection. Oral administration involving adsorption through the gastrointestinal tract uses compressed tablets, capsules, pills, troches, cahcets and pellets. Adminstration by the nasal or oral respiratory route may employ powdered or liquid polypeptide delivered as an aerosol. Nasal delivery includes administration by drops or sprays. Rectal administration may employ suppositories. The route of administration to be chosen will depend upon several variables, including the pharmacokinetic properties of MSP and the nature and severity of the condition being treated.

The invention provides for a pharmaceutical composition comprising a therapeutically effective amount of MSP and a pharmaceutically acceptable diluent, carrier, preservative, emulsifier, and/or solubilizer. Diluents include Tris, acetate or phosphate buffers; solubilizers include TWEEN, Polysorbate; carriers include human serum albumin; preservatives include thimerosol and benzyl alcohol; and anti-oxidants include ascorbic acid. MSP may also be conjugated with water soluble polymers (e.g., polyethylene glycol) using materials and method available to one skilled in the art in order to improve solubility, serum half-life, stability and bioavailability.

MSP may be present in formulations for use in particular delivery systems. As an example, MSP may be formulated for controlled delivery over a period of time. Such formulations include but are not limited to the following: encapsulation in a water insoluble polymer of hardened gelatin, methyl and ethyl celluloses, polyhydroxymethacrylate, hydroxypropylcellulose, polyvinylacetate and various waxes used alone or in combination; dispersion in an inert polymeric matrix of insoluble plastic, hydrophilic polymers, or fatty compounds; and coating with a water soluble polymer such as a shellac, wax, starch, cellulose acetate phthalate or polyvinylpyrrolidone. MSP may also be formulated for a targeted delivery system by entrapment within phospholipid vesicles. In a preferred embodiment, MSP may be incoporated in a cocoa butter or polyethylene glycol base for inclusion in a suppository for rectal delivery. In another preferred embodiment, MSP may be incorporated into a colon-specific drug release formulation such as that described in PCT Application No. WO 95/28963.

A more extensive survey of components commonly found in pharmaceutical compositions and formulations is presented in *Remington's Pharmaceutical Sciences,* 18th ed. A. R. Gennaro, ed. Mack, Easton, Pa. (1990), the relevant portions of which are incorporated by reference.

The invention also provides for a method for identifying substances capable of treating disorders of the gastrointestinal tract lining. The method comprises the steps of incubating the substance with isolated crypt cells under conditions which permit colony formation and obtaining stimulation of colony formation. The assay described in Example 1 provides a rapid method for screening substances that promote colony formation of crypt cells in vitro and allow one to rapidly identify substances that may be important in the proliferation of crypt cells and aid in the regeneration or repopulation of the intestinal epithelium. Materials suitable for screening include but are not limited to crude mixtures (e.g., conditioned medium, cell extracts and the like), purified polypeptides, carbohydrates and low molecular weight organic compounds wherein the latter may be assayed singly or in mixtures such as combinatorial libraries. It is anticipated that substances which promote colony formation will likely be involved in proliferation of colonic crypt cells.

The following examples are offered to more fully illustrate the invention, but are not construed as limiting the scope thereof.

EXAMPLE 1

Mouse Colon Crypt Colony Formation Assay

Mouse colon crypts were prepared as described in Whitehead et al. (In Vitro Cellular & Developmental Biology, 23, 436–442 (1987)). Mice were sacrificed with lethal dose of $CO_2$, and large intestines were isolated. The large intestine was cut longitudinally, rinsed with PBS containing 0.3 mg/ml L-Glutamine, 100 units/ml penicillin, 100 units/ml streptomycin (Buffer A), and sliced to 0.5 cm pieces. The sliced colon pieces were washed several times with buffer A in a 50 ml conical tube. The clean tissue was washed with the extraction buffer (0.5 mM DTT, 2 mM EDTA in buffer A), and then incubated with 10 ml of fresh extraction buffer for 1 hour. The extraction buffer was then removed, and tissue was washed with Solution A. The crypts were harvested by shaking the tissue in 5 ml of Solution A.

Harvested crypts were plated on collagen type IV coated 6 well plates (Collaborative Biomedical Products, Bedford, Mass.) at a density of 500 crypts per well in 4 ml medium (RPMI 1640, 0.3 mg/ml L-Glutamine, 100 units/ml penicillin, 100 units/ml streptomycin, and 10% fetal bovine serum (FBS; GIBCO-BRL. Gaithersburg, Md.). After 24 hours incubation at 37° C., colonies of attached cells were stained with crystal violet, and counted under microscope.

Figure 1:
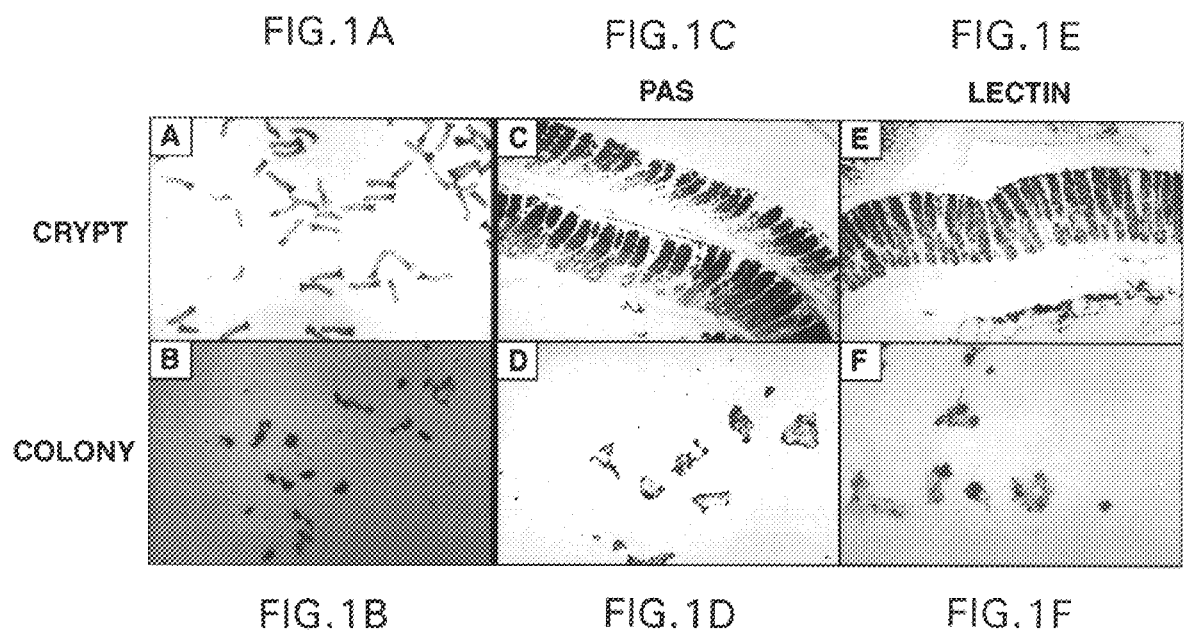
FIGS. 1A–1F. Visualization of mouse crypt epithelium. A) Crypts in suspension after isolation from adult mouse colon. B) Crypt cell colonies on collagen coated plate stained with crystal violet. C) and D) Mouse colon section and crypt colonies stained with McManus' Periodic Acid method. E) and F) Mouse colon section and crypt colonies stained with *Trichosantes kirilowii* for α/β-D-Galactosyl lectin.

To confirm that the cells in the colonies are derived from crypt epithelium, the colonies were stained with McManus' Periodic Acid-Schiff method and and *Trichosantes kirilowii* as described (Carson, *Histotechnology: A Self-Instructional Text* American Society of Clinical Pathologist Press pp. 158–160 (1990); (Falk et al. Am. J. Physiol. 266, G987–1003 (1994)). The colonies were compared to mouse colon paraffin sections stained with the same methods. The results of crypt cell staining are shown in FIG. 1 and reveal that both methods are specific for epithelial cells in the colon sections and stained positive for the colonies.

The formation of colonies is FBS dependent with 3–5 fold more colonies in medium containing 10% FBS than that without FBS. The increase of colony formation is not due to the general increase of protein in the medium, since the same effect was not observed when 10% BSA is used to substitute FBS. To test the effect of known protein factors in the assay, we substituted 10% FBS with 50 ng/ml of each factor tested in medium containing 0.1% BSA. The factors tested are shown in FIG. 2 and the results show that only neu differentiation factor-β1 (NDF-β1) gave the similar stimulation as FBS in the assay.

Figure 3:
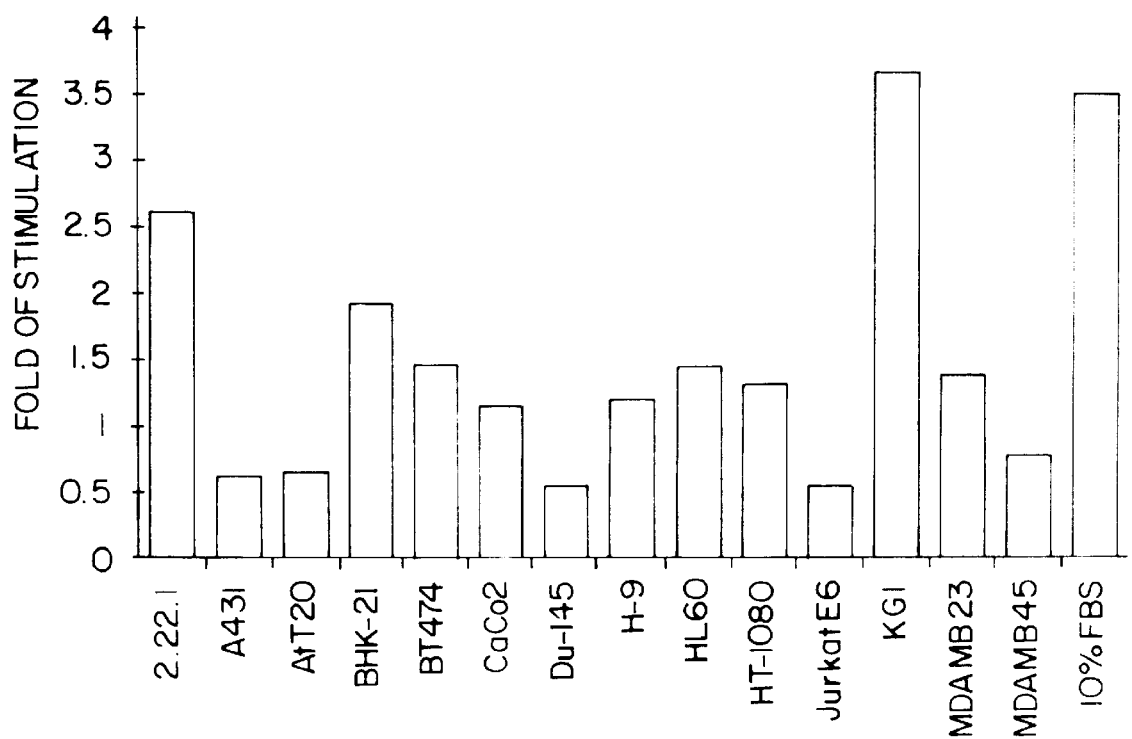
FIG. 3. Screening of cell line conditioned media for crypt colony formation activity. Conditioned media were tested as described in FIG. 2 at 0.25× of the original concentration. The activities were shown as fold of stimulation. 10% fetal bovine serum (FBS) was used as the positive control.
Figure 4A:
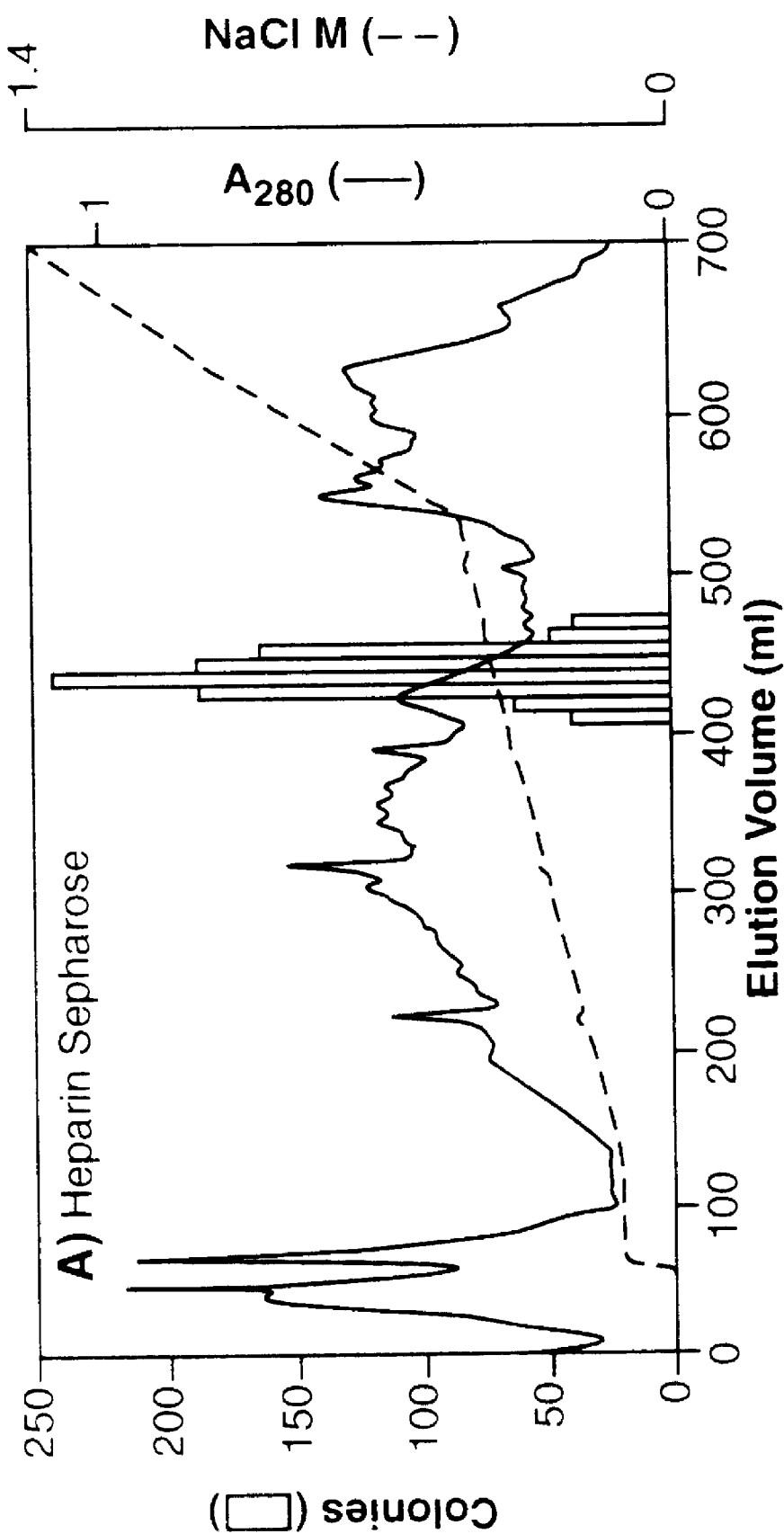
Figure 4B:
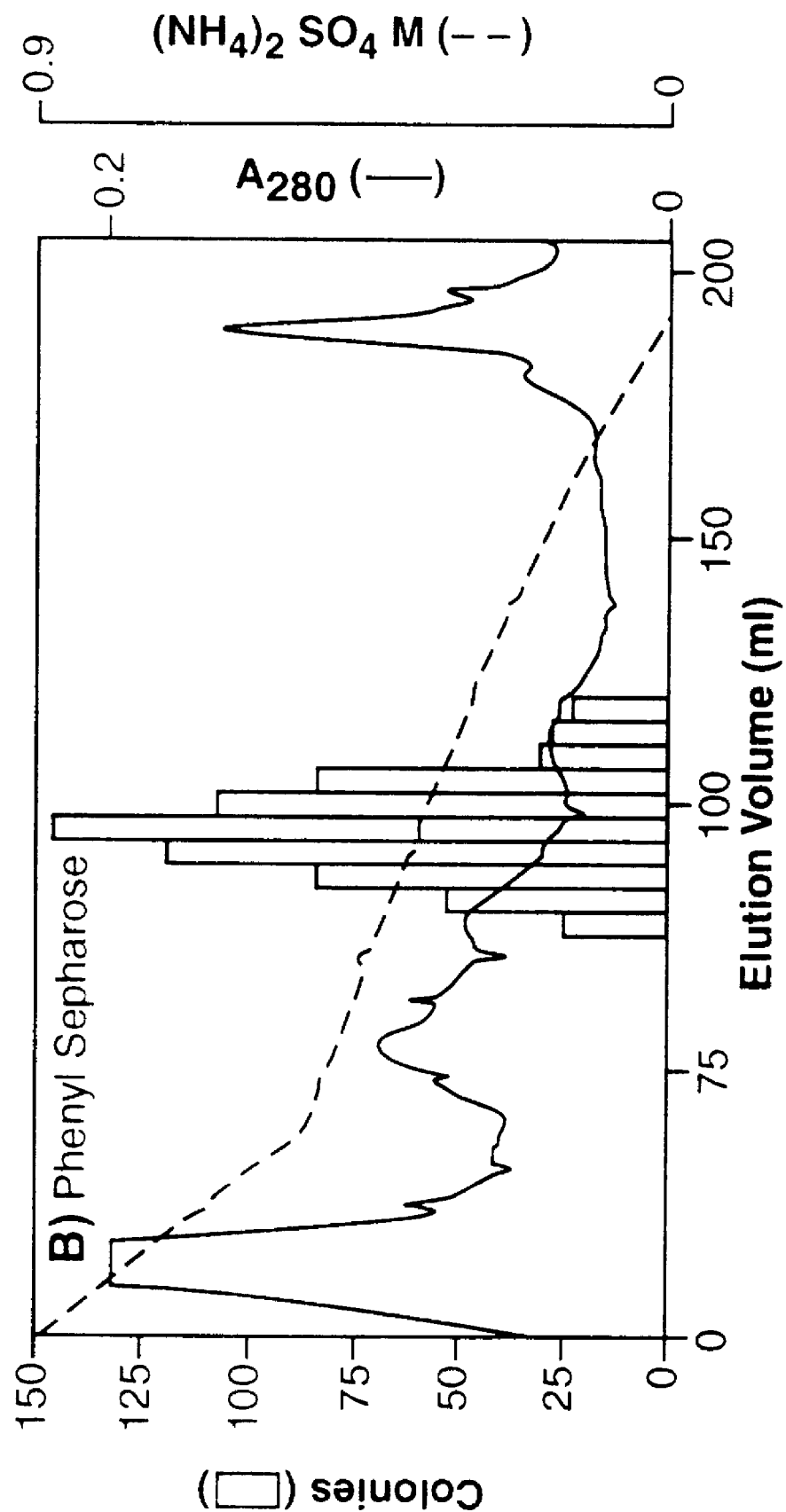

In order to identify novel factors which may stimulate colony formation by large intestine crypts, we screened conditioned media made from a number of different cell lines. The cell lines tested include 2.22.1, a mouse stromal cell line, A431 (available from the American Type Culture Collection, Rockville, Md., under accession no. CRL-1555), AtT20 (ATCC No. CCL-89), BHK-21 (ATCC No. CCL-20), BT-474 (ATCC No. HTB-20), CaCo2 (ATCC No. HTB-37), DU-145 (ATCC No. HTB-81), H-9 (ATCC No. HTB-176 ), HL-60 (ATCC No. CCL-240), HT-1080 (ATCC No. CCL-14), Jurkat E6 (ATCC No. TIB-152), KG-1 (ATCC No. CCL-246), MDA-MB-231 (ATCC No. HTB-26) and MDA-MB-45 (ATCC No. HTB-131). Generally, the cells were grown in their normal medium until 70% confluency or a density of $2 \times 10^6$/ml, and changed to medium containing 0.5% FBS. The conditioned media harvested after 3–7 days incubation. The conditioned media were tested in the crypt colony formation assay at 0.25× of original concentration. The results are shown in FIG. 3. In the bioassay, only conditioned medum from KG-1 cells gave stronger stimulation than 10% FBS.

EXAMPLE 2

Purification of Crypt Cell Colony Forming Factor from KG-1 Conditioned Medium

KG-1 cells were grown in RPMI 1640 medium supplemented with 0.3 mg/ml L-Glutamine, 100 units/ml penicillin, 100 units/ml streptomycin, and 10% FBS using 3 liter spinner for 3–5 days at 37° C. After reaching the density of $3 \times 10^6$ cells/ml, cells were harvested by centrifugation at 1000×g for 10 minutes. The cells were then resuspended in the same medium containing 0.5% FBS at the density of $1.5 \times 10^6$ cells/ml, and grown for 3 days at 37° C. The conditioned medium was harvested by removing the cells through centrifugation. A total of 150 liters of conditioned medium from 50 spinners were cleared by filtration through 0.45µ filters, and concentrated to 7.5 liters (20×) using a spiral-wound membrane cartridge (S1Y10, Amicon, Beverly, Mass.).

All protein purification steps performed by using a fast protein liquid chromatography system (Pharmacia, Piscataway, N.J.). The concentrated material were directly loaded onto a 70ml heparin-Sepharose column prebalanced to buffer A (20 mM $NaH_2PO_4$, pH7.2). The column was washed with buffer A, and the bound proteins were eluted with a gradient of NaCl (570 ml, from 0.05M to 0.7M), and 10 ml fractions were collected. Samples of 10 gl were used to tested the activity as described in the bioassay. The results show that the activity come out at the salt concentration of 0.2M. Active fractions from 9 column runs were pooled, and ammonium sulfate was added to reach a concentration of 1M. The material was loaded to a phenyl-Sepharose column (HR10/10). The column was developed with a 250 ml gradient of $(NH_4)_2SO_4$ (from 1M to no salt). Fractions of 5 ml were collected, and 2 µl of each fraction was used for bioassay. The activity was eluted with the salt concentration decreased to 0.4M. The active fractions from two column runs were pooled (30 ml), buffer exchanged, and concentrated by Centriplus 10 ultrafiltration (Amicon) to 5 ml in 20 mM Tris-HCl, pH7.5, and 0.005% Tween20. The material was loaded onto a Q-Sepharose column (HR5/2, Pharmacia) which was preequilibrated with the buffer (20 mM Tris-HCl, 0.005% Tween20). The bound proteins were eluted with a gradient of NaCl (30ml, from 0 to 1M) and 1 ml fraction were collected. Crypt colony formation assay was performed using 0.1 µl of each fractions. The activity appeared in fractions 8–11, with peak at fraction 9 and 10.

Samples of 5 µl from fractions 6–13 mixed with 5 µl of sample buffers (0.1M Tris-HCl, pH6.8, 40% glycerol, 0.004% bromphenol blue, 2% SDS, and with/or without 2% β-mercaptoethanol), and bioled for 5 minutes. The samples were electrophoresed on 2 8% polyacrylamide gels. The gels were stained with Coomassie blue. This analysis show a protein which correlated to the activity. This protein peared as a single band of 75 kd under non-reducing condition, and become two bands of 55 kd and 22 kd under reducing condition. There are also other visible protein bands, but none of these correlated with the activity observed.

EXAMPLE 3

Characterization of Crypt Colony Forming Factoras Bovine MSP

A. Protein sequence analysis

1. N-terminal sequence analysis of protein bands

Figure 5A:
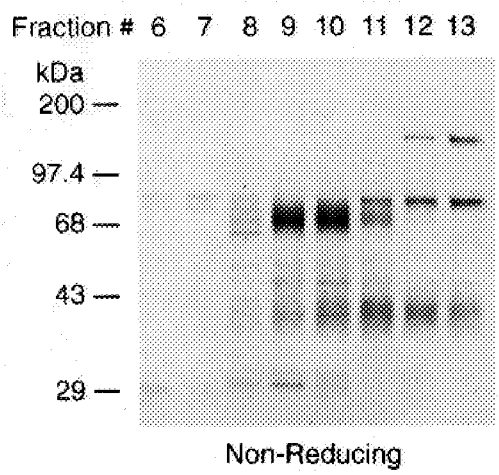
FIGS. 5A–5B. SDS-PAGE analysis of Q-Sepharose column fractions containing purified crypt colony forming activity. Q-Sepharose columns fraction 6–13 were electrophoresed on 8% SDS polyacrylamide gels. Five microliters of each sample were treated either with β-mercaptoethanol (2% v/v) (A) or without β-mercaptoethanol (B) for 5 minutes at 100° C. The resulting gels were stained with Coomassie blue.
Figure 5B:
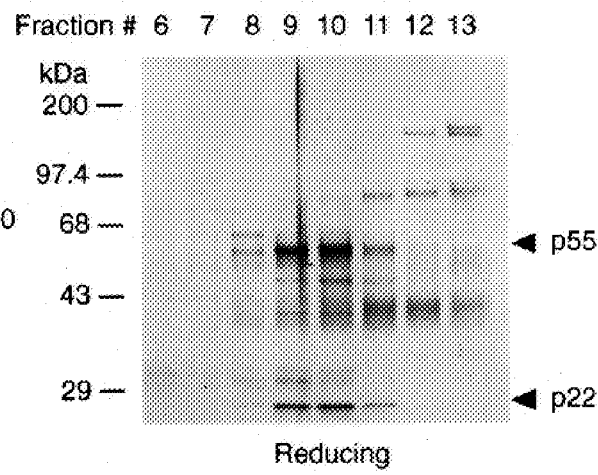

Purified crypt colony forming factor prepared as described in Example 2 was run on reducing SDS-PAGE using 10% Laemmli gels and then eletrophoretically transferred onto PVDF membrane (Problot, Applied Biosystems Inc., Foster City, Calif.) according to Fausset and Lu (Electrophoresis 12, 22–27 (1991)). After Coomassie blue staining, the stained protein band was cut out and directly loaded into an automatic protein sequencer (Model 477 liquid pulse sequencer, Applied Biosystems Inc.). Protein sequence analysis was performed using programs supplied by the manufacturer and the released phenyl thiohydantoinyl amino acids were analyzed on-line microbore C18 reverse-phase HPLC. A 29 amino acids sequence from the N-terminal of the small protein band was determined (FIGS. 5 and 6). The large protein band did not yield any sequence data, which suggests that the N-terminus is blocked.

2. Isolation and sequence analysis of tryptic peptides.

Purified factor was run on reducing SDS-PAGE as described above. The gel was then stained with 0.05% Coomassie brilliant blue G/20% methanol/5% acetic acid. Following destaining with 30% HPLC-grade methanol. The gel was washed overnight with HPLC-grade water and then the protein bands was cut out and subjected to in-gel trypsin digestion according to procedures described previously (Merewether et al. in *Techniques in Protein Chemistry VI*, pp. 153–160 (1995)). The trypsin digest was separated by reverse-phase HPLC on a 1090M HP liquid chromatography using a Synchrom C4 column (2.1×50 mm) column at a flow rate of 0.15 ml/min and detected at 215 and 280 nm. The elution was performed using a linear gradient of 0.1% trifluoroacetic acid in acetonitrile as described (Merewether et al, ibid). Aliquots of peptide fractions obtained were then subjected to sequence analysis as described above. A total of 11 peptide sequences were determined (FIG. 6). Analysis of the sequences shows a high degree of homology with regions of human MSP.

B. PCR analysis and DNA sequences

Figure 7:
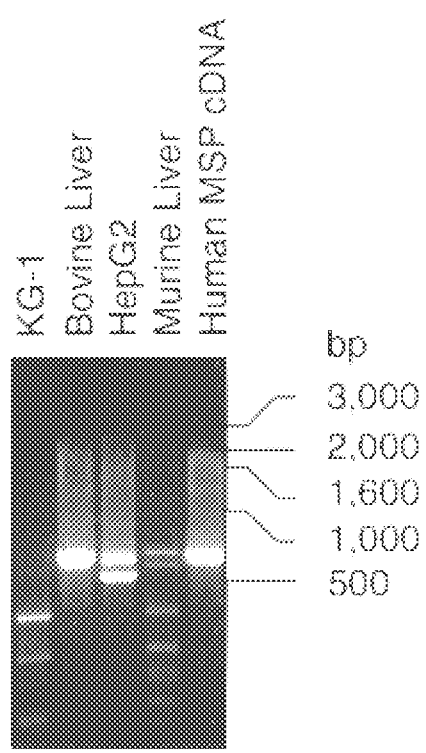
FIG. 7. PCR analysis of mRNA encoding the purified cyrpt colony forming activity. cDNAs were made from KG-1 poly A+ RNA, bovine liver polyA+ RNA, HepG2 total RNA, and murine liver total RNA. The cDNAs were then amplified using two degenerate oligonucleotides based on the amino terminal sequence of the purified protein and the sequence of the tryptic peptide T35.8B.
Figure 10:
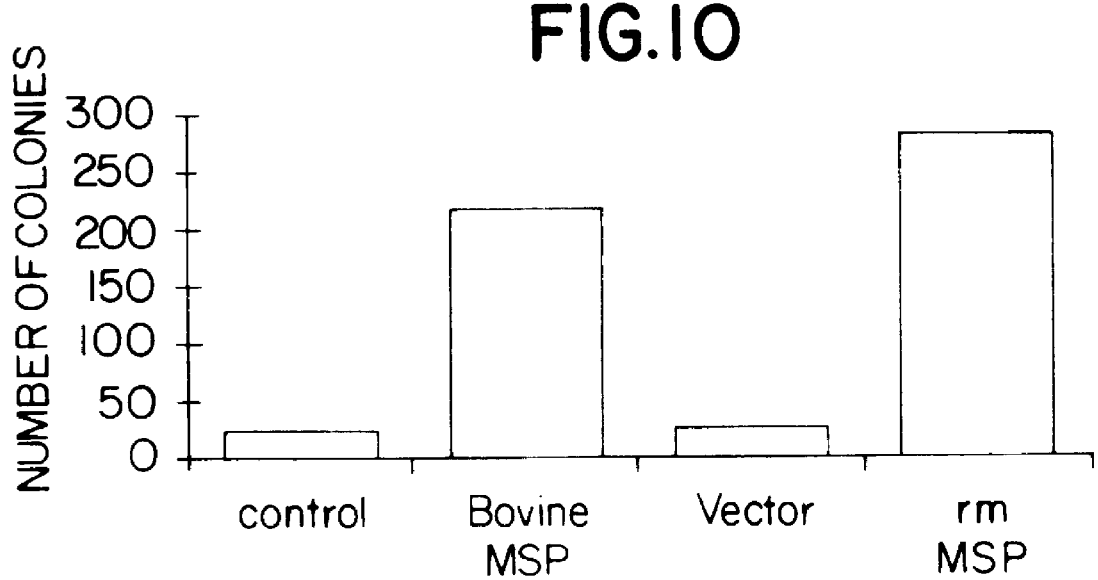
FIG. 10. Test of recombinant mouse MSP in crypt colony formation assay. Recombinant mouse MSP was produced in the conditioned medium of CHO cells and tested for stimulation of colony formation by crypt cells as described in FIG. 1. Purified bovine MSP (1 µg/ml) was used as the positive control, and conditioned medium from CHO cells transfected with vector was used as the negtive control. Both vector and recombinant mouse MSP were equal to 0.1× of the original conditioned medium.

To determine if the 75 kd protein is a product of the KG-1 cell line or is a bovine homolog of human MSP present in FBS, PCR analysis was performed using bovine liver polyA+ RNA (Clonetech Lab., Palo Alto, Calif.), KG-1 polyA+ RNA, total RNA from HepG2 cells (a human hepatocellular carcinoma cell line from ATCC) and mouse liver. PolyA+ RNA and total RNA were prepared by using a MRNA purification kit (Pharmacia), and by following the procedures described in the kit. The cDNAs were synthesized using the Superscript Preamplification System (GIBCO BRL). To make cDNA, 2 µg of polyA+ KG-1 and bovine liver RNA, and 5 µg of total HepG2 and mouse liver RNA were used in a total volume of 40 µl. The reactions were performed following the instructions provided in the kit. Two oligonucleotides were synthesized and used as the primers. The oligo 997-82:

CCICCICAIAAITGITGICCITG        (SEQ ID NO:1)

was designed complementary to a sequence which may encode the amino terminus of p22. The oligo 997-85:

GAIGCICAICCICAICAIGAIGCIAC        (SEQ ID NO:2)

was designed base on the sequence of T35.8b. PCR analysis was performed on a GeneAmp 9600 system (Perkin Elmer). The 501 reaction mixture contain 9 µl of cDNA, 0.5 µM of each primers, 1× buffer, 0.2 mM of each DNTP, and 3 units of Taq DNA polymerase (Perkin Elmer, Foster City, Calif.). For a positive control, 0.1 ng of human MSP cDNA (Degen et al., Biochemistry 3, 9781–9791 (1991)) was PCR amplified under the same condition. The reaction mixtures were heated at 95° C. for 4 minutes, then run 30 cycle of program A, 15 cycles of program B, and incubated at 72° C. for 10 minutes. Each cycle in program A contains 94° C. for 30 seconds, 54° C. decrease 0.2° C. for 30 seconds, and 72° C. for 60 seconds add 1 second. Each cycle in program B contains 94° C. for 30 seconds, 48° C. for 30 second, and 72° C. for 90 seconds. The resulting DNA was analyzed on a 0.8% agarose gel. As shown in FIG. 7, a fragment of 700 bp was observed in the PCR reaction using bovine liver polyA+ RNA. As expected, both human MSP cDNA and HepG2 total RNA give bands of same size. However, there is no clear DNA band of similar size produced by KG-1 polyA+ RNA. The sequence of the PCR fragment from bovine liver RNA was determined using the same two oligos as the primers. A sequence of 652 bp was obtained. The deduced amino acid sequence was shown in FIG. 10. The sequence share high homology with human MSP from amino acids 284–500. Four of the 12 peptide sequences are matched in this region. There are three differences between human and bovine MSP in the regions where the peptides matched. The peptide sequence agree with bovine MSP sequence in two of the three residues. In the last position, the peptide is different from both the bovine and human sequences.

EXAMPLE 4

The Effect of MSP on Colon Crypt Cells

Figure 9:
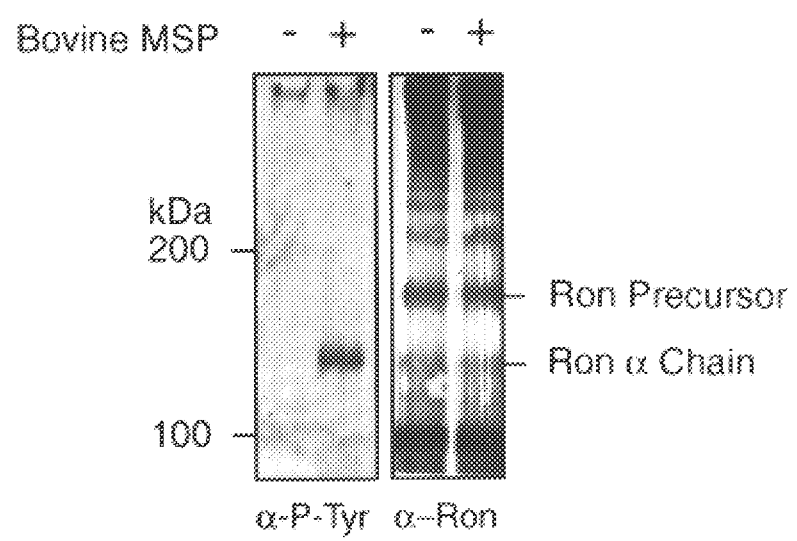
FIG. 9. Autophosphorylation of the ron receptor following MSP treatment of isolated crypts. Mouse colon crypt cells were treated with or without 100 ng/ml of bovine MSP for 20 minutes at 37° C., and lysed. The ron receptor protein was immunoprecipitated, and electrophoresed on a 6% acrylamide gel. The protein was transferred onto a nitrocellulose memberane, and blotted with an anti-phosphotyrosine (anti-PTyr) antibody (left panel). The membrane was then stripped and reblotted with an anti-RON antibody (right panel).

To determine the effect of MSP on the primary colon crypt cells, the activation of ron receptors on these cells was examined. Mouse colon crypts were isolated as described in Example 1. The total crypts (20,000) were divided into two tubes. The crypts were incubated with 1 ml of growth medium with/or without 100 ng/ml purified bovine MSP at 37° C. for 20 minutes. The crypts were collected by centrifugation, and lysed in 1 ml of lysis buffer (50 mM Tris HCl, pH 7.5, 150 mM NaCl, 1% NONIDET P-40, 0.5% sodium deoxycholate, 0.1% SDS, 0.1 mM dithiothreitol, 0.1 trypsin inhibitor units/ml aprotinin, 10 uM phenylmethyl-sulfonyl fluoride, and 0.4 mM vanadate). Immunoprecipitation and Western blot analysis were performed essentially as described (Harlow and Lane Antibodies: A Laboratory Manual, Cold Spring Harbor Laboratory Press, Cold Spring Harbor, N.Y. (1988)). The RON proteins were immunoprecipitated with an anti-mouse RON antibody. The lysates and antibodies were mixed gently at 4° C. for 1 hr. The immune complexes were collected with either Protein A SEPHAROSE (Pharmacia), and were then washed three times with lysis buffer. Bound proteins were released by boiling for 3 min in an equal volume of 2× protein sample buffer (0.1M Tris-HCl, pH 6.8, 40% glycerol, 0.004% bromophenol blue, 2% SDS, and 4% β-mercaptoethanol). The proteins were electrophoresed on a 6% polyacrylamide gel, and transfer to a nitrocellulose membrane. The filters were blocked overnight with 5% FBS and 3% Tween-20 in TBS, and were probed with anti-PTyr antibody (4G10, Upstate Biotechnology, Lake Placid, N.Y.) in the blocking solutions. The signals were visualized with peroxidase conjugated secondary antibodies and the ECL system (Amersham, Beverly, Mass.). The membrane was stripped and reblotted with anti-RON antibody. The results are shown on FIG. 9. Bovine MSP activated the RON proteins in the crypt cells by stimulating their autophosphorylation.

To confirm that the stimulation of colony formation in the bioassay was due to bovine MSP and not a contaminating protein, recombinant murine MSP was tested in the assay. To clone the mouse MSP cDNA, a 2266 bp fragment was amplified from cDNA made from mouse liver poly(A)+ RNA by using the following oligonucleotide primers:

ATCCTGAAGGGACAGATTTC        (SEQ ID NO:3)

and

TTTGAGAAGTCTTGACATCTC        (SEQ ID NO:4)

The primers were based on the published mouse MSP sequence (Degen et al. ibid.). Due to the presence of several mutations in the coding region of the PCR product, the cloned fragment was used as a probe to screen a mouse liver cDNA library (Clonetech). A positive clone with 2.2 kb insert was isolated and sequenced. The DNA sequence that was obtained indicated that this clone contains the coding region of mouse MSP except for the first two amino acids. To obtain the full-length cDNA, an adaptor including the optimal context for initiation of translation and the missing nucleotides was synthesized based upon the published sequence, and ligated to the 2.2 kb insert. The cDNA was subcloned into pcDNA3 vector (Invitrogen). The mouse MSP plasmid DNA was tranfected into COS-7 cells with lipofectamine transfection system (GIBCO BRL). Serum-free condition media were harvested two days after transfection. Conditioned medium made from COS-7 cells transfected with the vector DNA was used as the control. The conditioned media were tested in the bioassay described in Example 1. The results shown in FIG. 10 indicate that only the conditioned medium from cells transfected with mouse MSP stimulates colony formation.

While the present invention has been described in terms of the preferred embodiments, it is understood that variations and modifications will occur to those skilled in the art. Therefore, it is intended that the appended claims cover all such equivalent variations which come within the scope of the invention as claimed.

What is claimed is:

1. A method of treating disorders of the gastrointestinal tract lining in a mammal comprising administering a therapeutically effective amount of macrophage stimulating protein.

2. The method of claim 1 wherein the disorder results from chemotherapy or radiation therapy.

3. The method of claim 1 wherein the disorder results from inflammatory responses, autoimmune diseases, physical injury, ulcers or infection.

4. The method of claim 1 further comprising administering a therapeutically effective amount of IGF-1, IGF-2, EGF, TGF-α, acidic FGF, basic FGF, PDGF, KGF, IL-6 or IL-11.

5. The method of claim 1 wherein the protein is administered prior to, concurrent with, or after the onset of a disorder of the gastrointestinal tract lining.

6. The method of claim 5 wherein the protein is administered prior to or concurrent with chemotherapy or radiation therapy.

7. The method of claim 1 further comprising administering a therapeutically effective amount of a factor which stimulates hematopoiesis.

8. The method of claim 7 wherein the factor is EPO, G-CSF, MGDF, GM-CSF, SCF, IL-3 or IL-6.

9. A method of protecting, repairing or regenerating intestinal epithelium comprising administering a therapeutically effective amount of macrophage stimulating factor.

10. The method of claim 9 wherein the intestinal epithelium has been damaged or has the potential to be damaged by cancer therapy, physical injury or disease.

* * * * *

UNITED STATES PATENT AND TRADEMARK OFFICE
CERTIFICATE OF CORRECTION

PATENT NO. : 5,814,308

DATED : September 29, 1998

INVENTOR(S) : Zhang, Ke

It is certified that error appears in the above-identified patent and that said Letters Patent is hereby corrected as shown below:

Column 1, line 9, change "cell" to - - cells - -.

Column 8, line 36, change "singly" to - - singularly - -.

Column 9, line 3, change "and and" to - - and - -.

Column 10, line 4, change "10 gl" to - - 10 µl - -.

Column 10, line 28, change "bioled" to - - boiled - -.

Column 10, line 39, change "Factoras" to - - Factor As - -.

Signed and Sealed this

Twenty-fifth Day of May, 1999

Attest:

Q. TODD DICKINSON

*Attesting Officer*  *Acting Commissioner of Patents and Trademarks*

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid ( i x ) FEATURE:
        ( A ) NAME/KEY: misc_feature
        ( B ) LOCATION: 1..23
        ( D ) OTHER INFORMATION: /note= "N = Inosine"

( x i ) SEQUENCE DESCRIPTION: SEQ ID NO:1:

CCNCCNCANA ANTGNTGNCC NTG        23

( 2 ) INFORMATION FOR SEQ ID NO:2:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: other nucleic acid ( i x ) FEATURE:
        ( A ) NAME/KEY: misc_feature
        ( B ) LOCATION: 1..26
        ( D ) OTHER INFORMATION: /note= "N = Inosine"

( x i ) SEQUENCE DESCRIPTION: SEQ ID NO:2:

GANGCNCANC CNCANCANGA NGCNAC        26

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

ATCCTGAAGG GACAGATTTC        20

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

TTTGAGAAGT CTTGACATCT C                                                                                    21

( 2 ) INFORMATION FOR SEQ ID NO:5:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

```
Ser  Pro  Leu  Asn  Asp  Phe  Gln  Val  Leu  Arg
1                   5                        10
```

( 2 ) INFORMATION FOR SEQ ID NO:6:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

```
Phe  Pro  Asn  Asp  His  Lys
1                   5
```

( 2 ) INFORMATION FOR SEQ ID NO:7:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

```
Asn  Pro  Asp  Gly  Asp  Pro  Gly  Gly  Pro
1                   5
```

( 2 ) INFORMATION FOR SEQ ID NO:8:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:8:

```
Phe  Thr  Pro  Thr  Leu  Arg
1                   5
```

( 2 ) INFORMATION FOR SEQ ID NO:9:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:9:

```
Glu  Phe  Cys  Asp  Leu  Pro  Arg
```

( 2 ) INFORMATION FOR SEQ ID NO:10:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:10:

```
Asn  Pro  Asp  Gly  Ser  Glu  Ala  Pro  Trp  Cys  Phe  Thr  Gln  Arg
 1              5                        10
```

( 2 ) INFORMATION FOR SEQ ID NO:11:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:11:

```
Asn  Pro  Asp  Gly  Asp  Ser  His  Gly  Pro  Trp  Cys  Tyr
 1              5                        10
```

( 2 ) INFORMATION FOR SEQ ID NO:12:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:12:

```
Trp  Asp  Ala  Gln  Leu  Pro  His  Gln  His  Arg
 1              5                        10
```

( 2 ) INFORMATION FOR SEQ ID NO:13:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:13:

```
Trp  Asp  Leu  Gln  His  Pro  His  Pro  His  Pro  Phe  Glu  Pro  Gly  Lys
 1              5                        10                       15
```

( 2 ) INFORMATION FOR SEQ ID NO:14:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:14:

```
Cys  Gly  Ser  Glu  Ala  Gln  Pro  Gln  Gln  Glu  Ala  Thr  Thr  Leu  Asn  Cys
```

```
             1               5                   1 0                    1 5

Phe  Arg
```

( 2 ) INFORMATION FOR SEQ ID NO:15:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:15:

```
          Val  Val  Gly  Gly  Gln  Pro  Gly  Asn  Ser  Pro  Trp  Thr  Val  Ser  Leu  Arg
          1               5                   1 0                    1 5

Asn  Arg  Gln  Gly  Gln  His  Phe  Xaa  Gly  Gly  Ser  Leu  Val
                        2 0                   2 5
```

( 2 ) INFORMATION FOR SEQ ID NO:16:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:16:

```
          Leu  Glu  Arg  Pro  Val  Ile  Leu  Asn  Gln  Arg
          1               5                   1 0
```

( 2 ) INFORMATION FOR SEQ ID NO:17:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:17:

```
          Tyr  Val  Val  Pro  Pro  Gly  Thr  Arg
          1               5
```

( 2 ) INFORMATION FOR SEQ ID NO:18:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:18:

```
          Cys  Glu  Ile  Ala  Gly  Trp  Gly  Glu  Ser
          1               5
```

( 2 ) INFORMATION FOR SEQ ID NO:19:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear (i i) MOLECULE TYPE: protein (x i) SEQUENCE DESCRIPTION: SEQ ID NO:19:

```
Val  Ser  Val  Phe  Val  Asp  Trp  Lys  His  Lys
1              5                        10
```

(2) INFORMATION FOR SEQ ID NO:20:

(i) SEQUENCE CHARACTERISTICS:
        (A) LENGTH: 10 amino acids
        (B) TYPE: amino acid
        (C) STRANDEDNESS: single
        (D) TOPOLOGY: linear (i i) MOLECULE TYPE: protein (x i) SEQUENCE DESCRIPTION: SEQ ID NO:20:

```
Trp  Asp  Ala  Gln  Leu  Pro  His  Gln  His  Arg
1              5                        10
```

(2) INFORMATION FOR SEQ ID NO:21:

(i) SEQUENCE CHARACTERISTICS:
        (A) LENGTH: 14 amino acids
        (B) TYPE: amino acid
        (C) STRANDEDNESS: single
        (D) TOPOLOGY: linear (i i) MOLECULE TYPE: protein (x i) SEQUENCE DESCRIPTION: SEQ ID NO:21:

```
Asn  Pro  Asp  Gly  Ser  Glu  Ala  Pro  Trp  Cys  Phe  Thr  Gln  Arg
1              5                        10
```

(2) INFORMATION FOR SEQ ID NO:22:

(i) SEQUENCE CHARACTERISTICS:
        (A) LENGTH: 12 amino acids
        (B) TYPE: amino acid
        (C) STRANDEDNESS: single
        (D) TOPOLOGY: linear (i i) MOLECULE TYPE: protein (x i) SEQUENCE DESCRIPTION: SEQ ID NO:22:

```
Asn  Pro  Asp  Gly  Asp  Ser  His  Gly  Pro  Trp  Cys  Tyr
1              5                        10
```

(2) INFORMATION FOR SEQ ID NO:23:

(i) SEQUENCE CHARACTERISTICS:
        (A) LENGTH: 17 amino acids
        (B) TYPE: amino acid
        (C) STRANDEDNESS: single
        (D) TOPOLOGY: linear (i i) MOLECULE TYPE: protein (x i) SEQUENCE DESCRIPTION: SEQ ID NO:23:

```
Val  Val  Gly  Gly  Gln  Pro  Gly  Asn  Ser  Pro  Trp  Thr  Val  Ser  Leu  Arg
1              5                        10                       15
Asn
```

(2) INFORMATION FOR SEQ ID NO:24:

(i) SEQUENCE CHARACTERISTICS:
        (A) LENGTH: 217 amino acids
        (B) TYPE: amino acid
        (C) STRANDEDNESS: single (D) TOPOLOGY: linear (ii) MOLECULE TYPE: protein (xi) SEQUENCE DESCRIPTION: SEQ ID NO:24:

| Phe | Arg | Gly | Lys | Gly | Glu | Gly | Tyr | Arg | Gly | Thr | Val | Asn | Thr | Thr | Ala |
|---|---|---|---|---|---|---|---|---|---|---|---|---|---|---|---|
| 1 | | | | 5 | | | | | 10 | | | | | 15 | |
| Ala | Gly | Val | Pro | Cys | Gln | Arg | Trp | Asp | Ala | Gln | Leu | Pro | His | Gln | His |
| | | | 20 | | | | | 25 | | | | | 30 | | |
| Arg | Phe | Ala | Pro | Glu | Lys | Tyr | Ala | Cys | Lys | Asp | Leu | Arg | Glu | Asn | Phe |
| | | 35 | | | | | 40 | | | | | 45 | | | |
| Cys | Arg | Asn | Pro | Asp | Gly | Ser | Glu | Ala | Pro | Trp | Cys | Phe | Thr | Ser | Arg |
| | | 50 | | | | | 55 | | | | 60 | | | | |
| Pro | Gly | Met | Arg | Met | Ala | Phe | Cys | Tyr | Gln | Ile | Arg | Arg | Cys | Thr | Asp |
| 65 | | | | | 70 | | | | | 75 | | | | | 80 |
| Asp | Val | Arg | Pro | Glu | Asp | Cys | Tyr | His | Gly | Ala | Gly | Glu | Leu | Tyr | Arg |
| | | | | 85 | | | | | 90 | | | | | 95 | |
| Gly | Ser | Val | Ser | Lys | Thr | Arg | Lys | Gly | Ile | Arg | Cys | Gln | Asn | Trp | Ser |
| | | | 100 | | | | | 105 | | | | | 110 | | |
| Ala | Glu | Thr | Pro | His | Lys | Pro | Gln | Phe | Lys | His | Thr | Ser | Ala | Pro | His |
| | | 115 | | | | | 120 | | | | | 125 | | | |
| Thr | Pro | Leu | Glu | Glu | Asn | Phe | Cys | Arg | Asn | Pro | Asp | Gly | Asp | Ser | His |
| | 130 | | | | | 135 | | | | | 140 | | | | |
| Gly | Pro | Trp | Cys | Tyr | Thr | Thr | Asp | Pro | Gly | Thr | Pro | Phe | Asp | Tyr | Cys |
| 145 | | | | | 150 | | | | | 155 | | | | | 160 |
| Ala | Leu | Arg | Arg | Cys | Asp | Asp | Gln | Gln | Pro | Ser | Ile | Leu | Glu | Thr | |
| | | | | 165 | | | | 170 | | | | | 175 | | |
| Ala | His | Gln | Val | Leu | Phe | Asp | Lys | Cys | Gly | Lys | Arg | Val | Thr | Arg | Val |
| | | | 180 | | | | | 185 | | | | | 190 | | |
| Asp | Pro | Leu | His | Ser | Lys | Leu | Arg | Val | Val | Gly | Gly | Gln | Pro | Gly | Asn |
| | | 195 | | | | | 200 | | | | | 205 | | | |
| Ser | Pro | Trp | Thr | Val | Ser | Leu | Arg | Asn | | | | | | | |
| | 210 | | | | | 215 | | | | | | | | | |

(2) INFORMATION FOR SEQ ID NO:25:

(i) SEQUENCE CHARACTERISTICS:
        (A) LENGTH: 217 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:25:

| Phe | Arg | Gly | Lys | Gly | Glu | Gly | Tyr | Arg | Gly | Thr | Ala | Asn | Thr | Thr | Thr |
|---|---|---|---|---|---|---|---|---|---|---|---|---|---|---|---|
| 1 | | | | 5 | | | | | 10 | | | | | 15 | |
| Ala | Gly | Val | Pro | Cys | Gln | Arg | Trp | Asp | Ala | Gln | Ile | Pro | His | Gln | His |
| | | | 20 | | | | | 25 | | | | | 30 | | |
| Arg | Phe | Thr | Pro | Glu | Lys | Tyr | Ala | Cys | Lys | Asp | Leu | Arg | Glu | Asn | Phe |
| | | 35 | | | | | 40 | | | | | 45 | | | |
| Cys | Arg | Asn | Pro | Asp | Gly | Ser | Glu | Ala | Pro | Trp | Cys | Phe | Thr | Leu | Arg |
| | | 50 | | | | | 55 | | | | 60 | | | | |
| Pro | Gly | Met | Arg | Ala | Ala | Phe | Cys | Tyr | Gln | Ile | Arg | Arg | Cys | Thr | Asp |
| 65 | | | | | 70 | | | | | 75 | | | | | 80 |
| Asp | Val | Arg | Pro | Gln | Asp | Cys | Tyr | His | Gly | Ala | Gly | Glu | Gln | Tyr | Arg |
| | | | | 85 | | | | | 90 | | | | | 95 | |
| Gly | Thr | Val | Ser | Lys | Thr | Arg | Lys | Gly | Val | Gln | Cys | Gln | Arg | Trp | Ser |

-continued

|   |   |   |   |   | 100 |   |   | 105 |   |   |   | 110 |   |   |
|---|---|---|---|---|---|---|---|---|---|---|---|---|---|---|
| Ala | Glu | Thr 115 | Pro | His | Lys | Pro | Gln 120 | Phe | Thr | Phe | Thr | Ser 125 | Glu | Pro | His |
| Ala | Gln 130 | Leu | Glu | Glu | Asn | Phe 135 | Cys | Arg | Asn | Pro | Asp 140 | Gly | Asp | Ser | His |
| Gly 145 | Pro | Trp | Cys | Tyr | Thr 150 | Met | Asp | Pro | Arg | Thr 155 | Pro | Phe | Asp | Tyr | Cys 160 |
| Ala | Leu | Arg | Arg | Cys 165 | Ala | Asp | Asp | Gln | Pro 170 | Pro | Ser | Ile | Leu | Asp 175 | Pro |
| Pro | Asp | Gln | Val 180 | Gln | Phe | Glu | Lys | Cys 185 | Gly | Lys | Arg | Val | Asp 190 | Arg | Leu |
| Asp | Gln | Arg 195 | Arg | Ser | Lys | Leu | Arg 200 | Val | Val | Gly | Gly | His 205 | Pro | Gly | Asn |
| Ser | Pro 210 | Trp | Thr | Val | Ser | Leu 215 | Arg | Asn |   |   |   |   |   |   |   |